(12) United States Patent
Bödewadt et al.

(10) Patent No.: US 10,022,128 B2
(45) Date of Patent: Jul. 17, 2018

(54) CONE EXPANDING COLLAPSIBLE MEDICAL DEVICE

(71) Applicant: COOK MEDICAL TECHNOLOGIES LLC, Bloomington, IN (US)

(72) Inventors: Tue Thuren Bödewadt, Solroed Strand (DK); Christina Rauff Hansen, Copenhagen (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 301 days.

(21) Appl. No.: 14/996,286

(22) Filed: Jan. 15, 2016

(65) Prior Publication Data
US 2016/0206319 A1 Jul. 21, 2016

(30) Foreign Application Priority Data

Jan. 16, 2015 (GB) .................. 1500735.4

(51) Int. Cl.
*A61B 17/12* (2006.01)
*A61F 2/01* (2006.01)

(52) U.S. Cl.
CPC .. *A61B 17/12109* (2013.01); *A61B 17/12031* (2013.01); *A61B 17/12172* (2013.01); *A61B 17/12177* (2013.01); *A61F 2/01* (2013.01); *A61B 2017/12054* (2013.01); *A61F 2002/016* (2013.01); *A61F 2230/008* (2013.01)

(58) Field of Classification Search
CPC ........ A61B 17/12109; A61B 17/12177; A61B 17/12031; A61B 17/12172; A61B 2017/12054; A61F 2/01; A61F 2230/008; A61F 2002/016
See application file for complete search history.

(56) References Cited

U.S. PATENT DOCUMENTS

| | | | |
|---|---|---|---|
| 4,643,184 A | 2/1987 | Mobin-Uddin |
| 4,832,055 A | 5/1989 | Pelestrant |
| 4,990,156 A | 2/1991 | Lefebvre |
| 5,108,420 A | 4/1992 | Marks |

(Continued)

FOREIGN PATENT DOCUMENTS

WO WO2007/110195 10/2007

OTHER PUBLICATIONS

Combined Search and Examination Report for Application No. GB1500735.4, dated Jun. 12, 2015.

*Primary Examiner* — Julian W Woo
(74) *Attorney, Agent, or Firm* — Brinks Gilson & Lione

(57) ABSTRACT

A vascular occluder includes first and second conical members disposed in opposing relation and which have tooth-shaped wide ends. The conical members are coupled to one another by a coupling element, which may be a cannula or rod. The conical members are formed of a membrane which has a thickness which increases towards the narrow ends and decreases towards the toothed elements. The toothed elements are preferably self-supporting within a vessel and avoid folds within the occluder membrane, which may otherwise result in leakage of blood around the device. The device may be provided with a supporting frame which may be at least partially embedded within the membrane. The membrane is preferably made of silicone.

19 Claims, 6 Drawing Sheets

(56) References Cited

U.S. PATENT DOCUMENTS

| | | | |
|---|---|---|---|
| 5,456,693 A | | 10/1995 | Conston et al. |
| 5,683,411 A | * | 11/1997 | Kavteladze ........ A61B 17/0057 |
| | | | 606/200 |
| 6,013,093 A | | 1/2000 | Nott et al. |
| 6,143,015 A | | 11/2000 | Nobles |
| 6,193,748 B1 | * | 2/2001 | Thompson ....... A61B 17/12022 |
| | | | 623/1.3 |
| 6,589,256 B2 | * | 7/2003 | Forber ............. A61B 17/12022 |
| | | | 606/151 |
| 7,316,695 B2 | * | 1/2008 | Mialhe ............... A61B 17/0057 |
| | | | 606/158 |
| 8,764,772 B2 | * | 7/2014 | Tekulve ........... A61B 17/12022 |
| | | | 606/151 |
| 9,173,659 B2 | * | 11/2015 | Bodewadt ........ A61B 17/12109 |
| 9,364,354 B2 | * | 6/2016 | Ben-Muvhar ............. A61F 2/91 |
| 9,687,242 B2 | * | 6/2017 | Hendriksen ...... A61B 17/12022 |
| 9,844,653 B2 | * | 12/2017 | Conder ................ A61M 29/00 |
| 9,848,883 B2 | * | 12/2017 | Cragg ............. A61B 17/12172 |
| 2002/0065545 A1 | | 5/2002 | Leonhardt et al. |
| 2002/0198563 A1 | | 12/2002 | Gainor et al. |
| 2005/0065546 A1 | | 3/2005 | Corcoran et al. |
| 2005/0065547 A1 | | 3/2005 | Marino et al. |
| 2005/0165441 A1 | | 7/2005 | McGuckin, Jr. et al. |
| 2005/0228434 A1 | | 10/2005 | Amplatz et al. |
| 2006/0074484 A1 | | 4/2006 | Huber |
| 2010/0114299 A1 | | 5/2010 | Ben Muvhar et al. |
| 2011/0282274 A1 | | 11/2011 | Fulton, III |
| 2011/0301630 A1 | | 12/2011 | Hendriksen et al. |
| 2013/0096550 A1 | | 4/2013 | Hill |

* cited by examiner

CONE EXPANDING COLLAPSIBLE MEDICAL DEVICE

RELATED APPLICATIONS

This application claims the benefit of priority under 35 U.S.C. § 119(a) to Great Britain Patent Application No. GB 1500735.4, filed on Jan. 16, 2015, which is incorporated by reference here in its entirety.

TECHNICAL FIELD

The present invention relates to a collapsible medical device for vascular implantation, in the preferred embodiment to a vascular occluder.

BACKGROUND ART

There is a plurality of medical conditions for which it is desired to occlude a body vessel, be it temporarily or permanently. Occlusion devices for this purpose could be categorized into two different types, a first which provides instant occlusion of a vessel and a second which relies on embolization. Instant occluders provide a physical barrier spanning across the diameter of the vessel and can achieve near instantaneous occlusion. Such devices, however, must remain reliably in place without migration or leakage through the occluder, between the occluder and the vessel wall. Embolization occluders provide a device which has at least one clotting promoter, such as a coil possibly with thrombogenic fibres attached thereto, and rely on the formation of a thrombus in the vessel to achieve occlusion. While these latter occluders take time to achieve occlusion, they tend to have high reliability once successfully deployed. In the case of embolization coils, it is often necessary to implant a series of coils in order to achieve the required degree of occlusion.

Examples of prior art occlusion devices can be found in U.S.-2005/0,065,547, U.S. Pat. No. 4,643,184, U.S. Pat. No. 4,832,055, U.S. Pat. No. 5,108,420, U.S. Pat. No. 5,456,693, U.S. Pat. No. 6,143,015, U.S.-2002/0,065,545, U.S.-2002/0,198,563, U.S.-2005/0,065,546, U.S.-2005/0,165,441, U.S.-2005/0,228,434, U.S.-2006/0,074,484, U.S.-2010/0,114,299, U.S.-2011/0,282,274, U.S.-2013/0,096,550 and WO-2007/110,195.

DISCLOSURE OF THE INVENTION

The present invention seeks to provide an improved medical device for vascular implantation, in the preferred embodiment to an improved vascular occluder.

According to an aspect of the present invention, there is provided a collapsible medical device including: first and second conical members, each having a wide end and a narrow end; a connecting element coupled to the first and second conical members, the connecting element being fixed to the narrow end of each conical member, the first and second conical members being arranged such that their narrow ends are adjacent one another and their wide ends face opposing directions; the first and second conical members including a conical membrane having a thickness decreasing from the narrow end to the wide end; the wide end of each conical member being tooth shaped.

A medical device of such a structure can be configured as an occluder. When placed in a vessel one of the conical members will be disposed against the flow of blood or other bodily fluid, whereupon the pressure of blood acts to bias the conical element into an open position and to press it against the walls of the vessel. The toothed cone ends, it has been found, are able to sit against the vessel wall with little risk of leakage around the conical member and are also able to fit reliably into a range of vessel diameters. A device having a straight edge can ruffle, leading to loss of the seal to the vessel wall.

Furthermore, the tapering nature of the membrane forming the conical membranes contributes to their flexibility, conformability with the vessel and can also enable to device to be compressed to a small diameter useful for deployment in or through small size vessels. Greater flexibility enhances the fit of the wide end to the vessel wall.

Preferably, the device is an occluder and the membrane of the first and second conical members is an occluding element. In other embodiments the membranes may be porous to blood plasma and able thereby to act as filter elements.

Advantageously, the membrane of the conical members is self-supporting. This enables the manufacture of devices requiring no supporting structure, useful for devices for very small vessels including the cerebral vessels.

The conical membranes may be formed of a flexible and non-degradable material.

Preferably, the conical membranes are formed of a polymeric material, most preferably of silicone. Silicone, it has been found, allows the manufacture of devices with very thin walls and of very flexible devices which can be compressed to a very small footprint. Moreover, silicone generates a good opening force in the cones, for reliable deployment in a vessel. It can also be self-supporting.

In some embodiments the medical device may include at least one frame element coupled to the conical members. Such a frame element may be particularly advantageous for devices for larger vessels.

The device may include first and second frame elements coupled respectively to the first and second conical members.

In another embodiment, a single frame element spans across the first and second conical members. Such a frame element may include a medial constraining ring disposed between the first and second conical members.

The or each frame element may be made of a metal or metal alloy and/or of shape memory material. A nickel titanium alloy such as Nitinol is particularly suitable.

In some embodiments, the or each frame element may extend beyond the wide ends of the conical members. The or each frame element may include a diamond shaped portion extending beyond the conical members. Such an extension to the frame element is useful in fixing the device, particularly in larger vessels, and allows for endothelialisation around the exposed frame portions.

The or each frame element is at least partially embedded in the membrane of the conical members. This avoids the need for securing elements, such as sutures, and also reduces the thickness of the device, optimising its compressibility for deployment purposes.

In an embodiment, the connecting element is a rod. In another embodiment, the connecting element is a cannula having a lumen therein, which enables the device to be deployed over a guide wire. In this latter embodiment, there may be provided at least one closure element disposed to close the lumen of the cannula. The at least one closure element may be an occlusion element.

Other features and advantages will become apparent from the specific description which follows.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
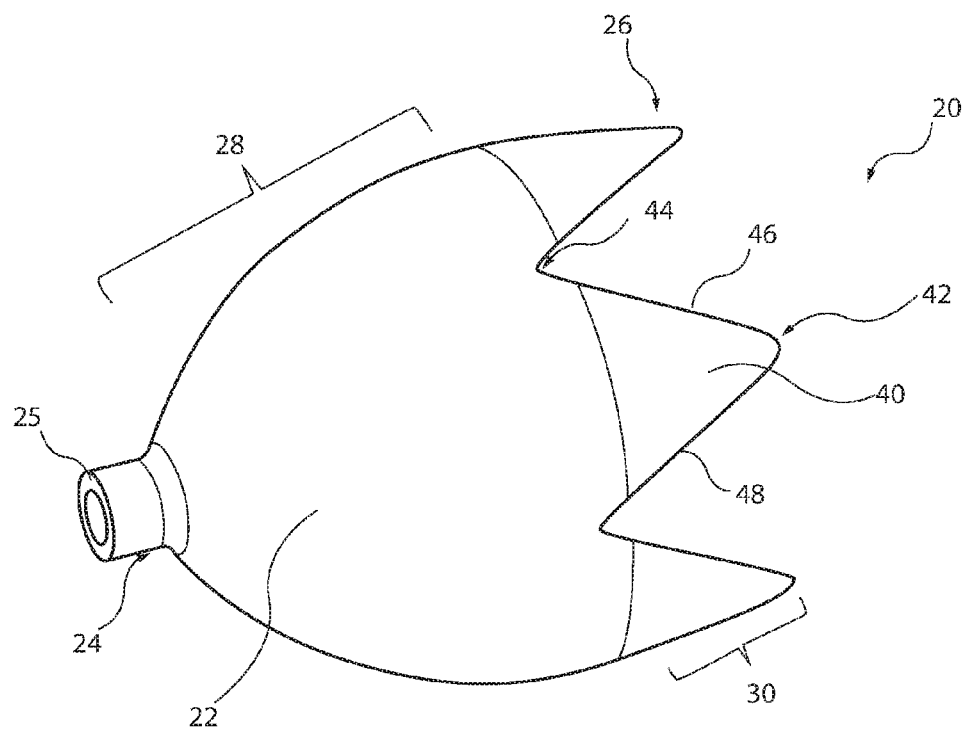
FIG. 1 is a perspective view of an embodiment of conical occluder member.

The skilled person will appreciate that the drawings are schematic only and simplified in order to depict the principal elements of the devices shown. The elements shown in the drawings are also not to scale. Suitable sizing and scaling will be readily determinable by the skilled person having regard to common knowledge in the art.

The preferred embodiments described below and shown in the drawings are related to an occluder device for occluding a body vessel. The teachings herein are not, however, limited to occlusion devices as they could equally be applied to other devices. For example, the conical members could be made porous or with apertures allowing the passage of blood plasma but which are small enough to trap debris such as thrombi formations, thereby to act as filtering elements. The teachings herein are therefore applicable to a variety of implantable medical devices.

Referring first to FIG. 1, this shows in schematic form an embodiment of conical member 20 which is configured as an occluder, in other words which is formed of an occluding or impermeable membrane 22. The conical member 20 has a narrow end 24 which terminates in a cylindrical coupling flange or collar 25, and a wide end 26. A first section 28 of the member 20 curves in concave manner from the narrow end 24 and in the preferred embodiment has a spherical or ovoid (oval) shape. A second section 30 extends from the first section 28 to the wide end of the member 20 and has a more uniform diameter, either to be generally cylindrical or to be only slightly tapering, to widen or narrow towards the open extremity 26. The section 30 will generally rest against the internal wall of a vessel to provide a fluid tight seal.

The skilled person will appreciate that the term "conical" used herein refers to a shape which tapers towards one end and which may have, as in the preferred embodiment, an outer form which is rounded in the longitudinal direction of the device, that is with a diameter which does not vary linearly along the taper but which has a reducing radius or slope.

The open extremity, or wide end, 26 of the member 20 is toothed shaped, that is has an end wall which in this embodiment has a zigzag shape when viewed in side elevation. The tooth shape provides a series of circumferentially disposed teeth elements 40 having their apices 42 at the open extremity of the conical member 20 and which widen to valleys 44, which are located in this embodiment at the end of the second portion 40, that is adjacent the first portion 28. The teeth elements 40 have substantially straight sides 46, 48 in the embodiment shown, although these could be curving in other embodiments. Similarly, the apices and valleys are only slightly rounded in the embodiment shown but in other embodiments could have greater rounding.

Figure 2:
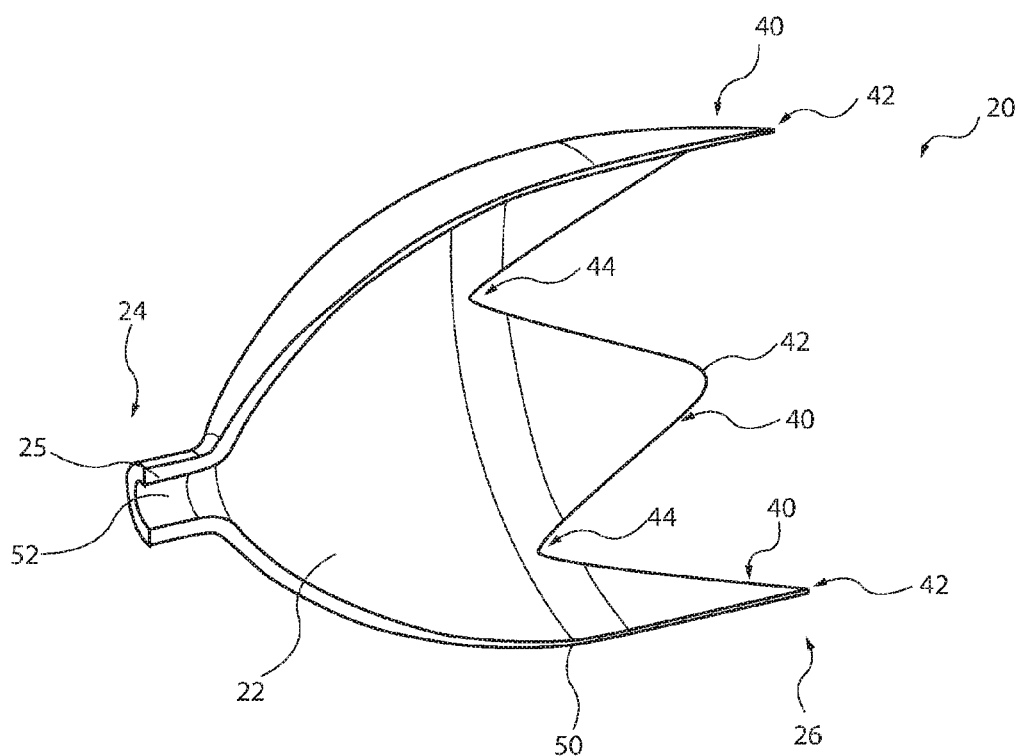
FIG. 2 is a cross-sectional view in perspective of the occluder member of FIG. 1.

The teeth elements 40 are curved in the circumferential direction of the member 20, as will be apparent in particular from FIG. 2.

It is preferred that the member 20 is formed as a unitary element, including the collar 25. The member 20 in this embodiment is formed of a membrane 22 which is impervious so as to act as an occluder in use. The membrane is preferably flexible and of non-degradable biocompatible material. Preferred materials are polymers and most preferably of a rubber-like consistency for resiliency. Silicone is most preferred as this is highly biocompatible, does not degrade, can generate sufficient opening force and can be made very thin.

Referring now to FIG. 2, this shows the conical member 20 in cross-section. The membrane 22 has a wall 50 which tapers in thickness from the narrow end 24 to the wide end 26, that is which gets thinner in the direction of widening of the member 20. It is preferred that the wall thickness of the member 22 at the teeth elements 40 is sufficient to enable to teeth elements 40 to be self-supporting in the configuration shown in FIGS. 1 and 2, that is without the need for any other support or frame elements. The wall 50 is thickest at the collar 25, which has a lumen 52 running therethrough.

It will be appreciated that in the preferred embodiment the conical member 20 is substantially circular in axial cross-section throughout its length.

Figure 3:
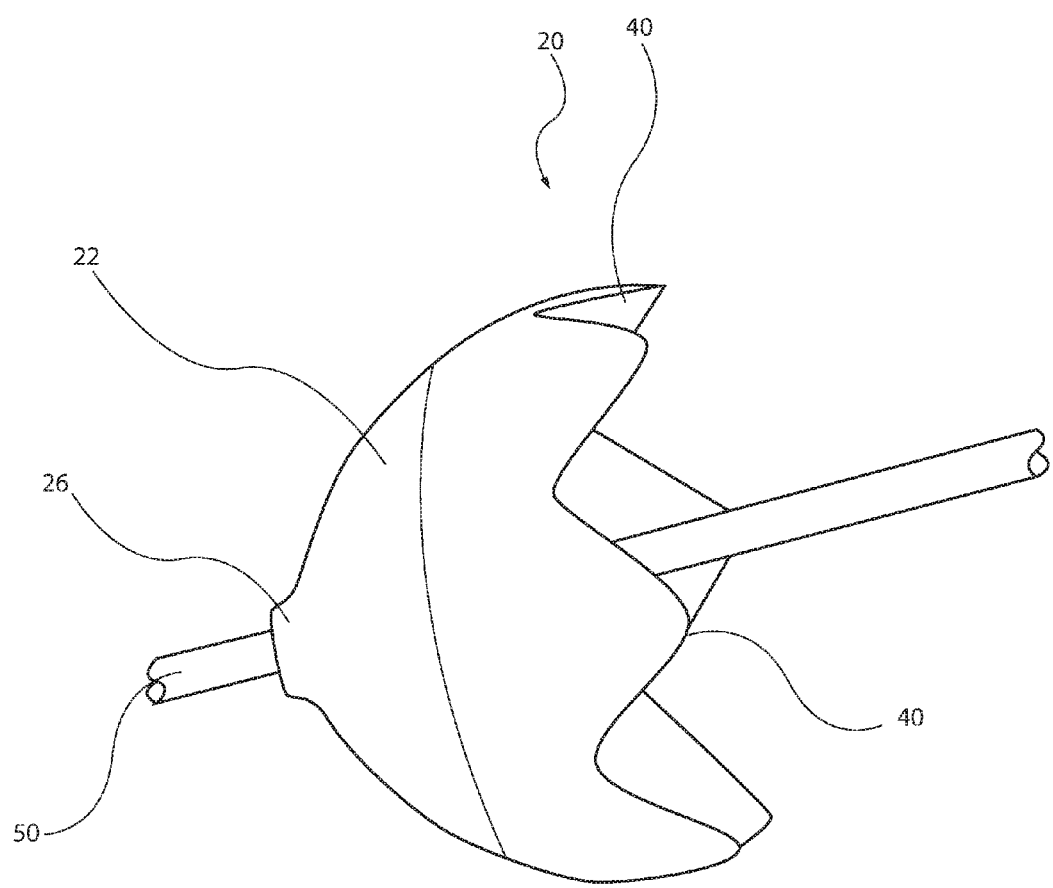
FIG. 3 is a photograph of a prototype occluder member formed from silicone.

Referring now to FIG. 3, this shows a photograph of a prototype occluder cup or conical member 20 formed solely of silicone. The occluder member 20 has a shape broadly similar to the embodiment of FIGS. 1 and 2, although the outer profile is gently and uniformly rounded along its entire length in the longitudinal direction, as will be apparent from FIG. 3.

As can be seen, the occluder member is sub-supported in its open or deployed configuration, achieved by the natural springiness of the silicone material.

The occluder member is disposed on a cannula 50, which could be used in practical embodiments of the device taught herein. The cannula 50 may be made of a metal or metal alloy, with the collar 26 bonded thereto, for example with adhesive or the like. Equally, the cannula 50 could be made of a polymeric material.

Figure 4:
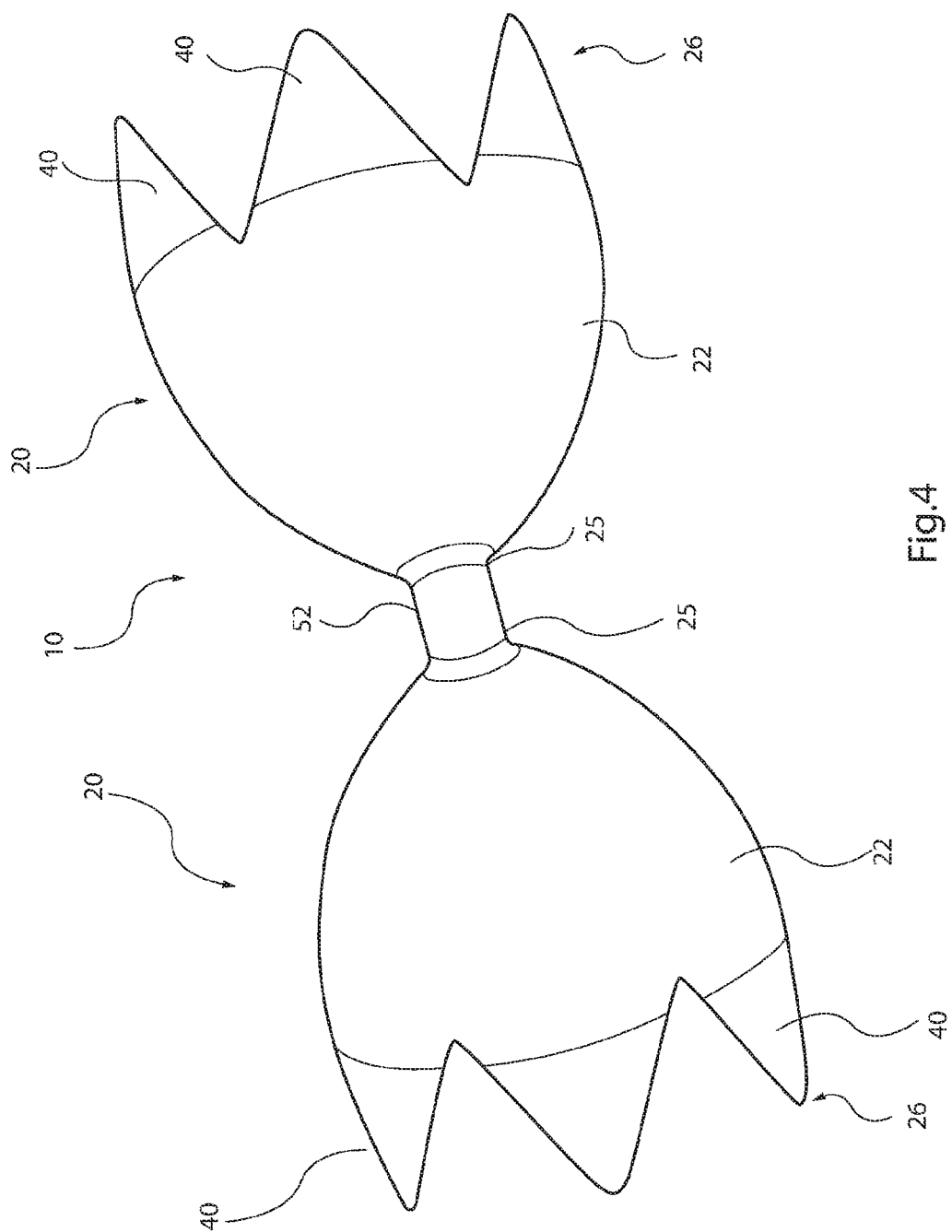
FIG. 4 is a schematic diagram of a medical device formed of two of the occluder members of FIG. 1 arranged in back-to-back configuration.

Referring now to FIG. 4, this shows the medical device in the basic form in which it will be provided, namely with a pair of occluding members 20 disposed in opposing relation, that is with their narrow ends 24 or collars 26 adjacent one another and with their wide ends 26 facing in opposing directions. The two conical members 20 are coupled to one another by a connecting element 52, which may be a rigid cannula of the type shown in FIG. 3 or a flexible element. The connecting element 52 may be a rod. In other embodiments the element 52 is a cannula having a lumen therein, providing a passageway through the conical occluder elements 20 and in effect through the device 10, which can be used for the passage of a guide wire, enabling the device 10 to be deployed over the wire. When the connecting element 52 is a cannula, it may be provided with at least one closure element to close the cannula after deployment of the device 10. The closure element could be thrombogenic fibres, a valve arrangement, or the like.

It will be appreciated that the device 10 shown in FIG. 4 is symmetrical along the longitudinal axis, which enables the device 10 to be disposed within the patient in either orientation, which can facilitate the assembly procedure as well as the deployment procedure, allowing the device to be deployed from either direction in a vessel. Moreover, the device 10 has natural orientational stability as the two conical elements will support one another within the vessel, thereby ensuring that the toothed fingers or elements 40 rest properly against the vessel wall, with the longitudinal axis of the device 10 extending along the centreline of the vessel.

The embodiments shown with reference to FIGS. 1 to 4 all have conical members 20 which are self-supporting, that is which do not have any supporting structure beyond the membrane or material 22 forming the conical members 20. The person skilled in the art will appreciate that in some instances strengthening elements may be provided within the conical members 20, such as a suitable framework or the like either disposed within the membranes 22 or at least partially embedded within the membranes.

Figure 5:
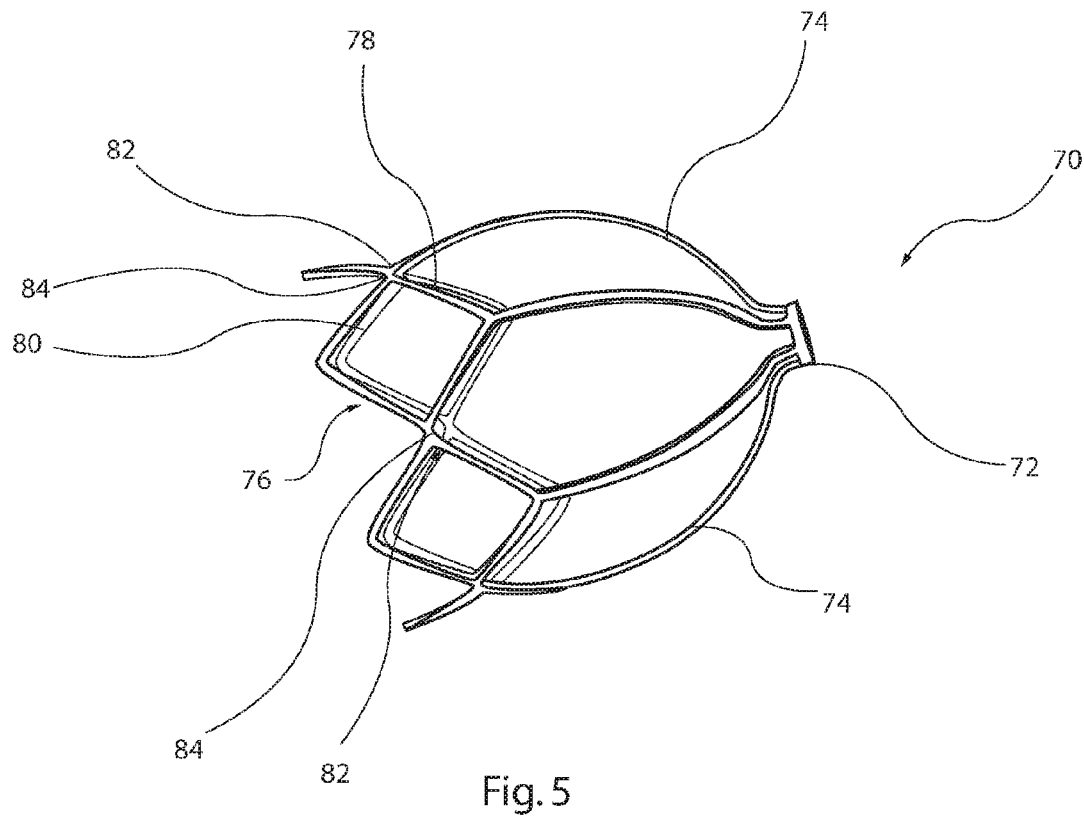
FIGS. 5 and 6 are, respectively, side elevational and perspective views of an embodiment of frame for the occluder members taught herein.
Figure 6:
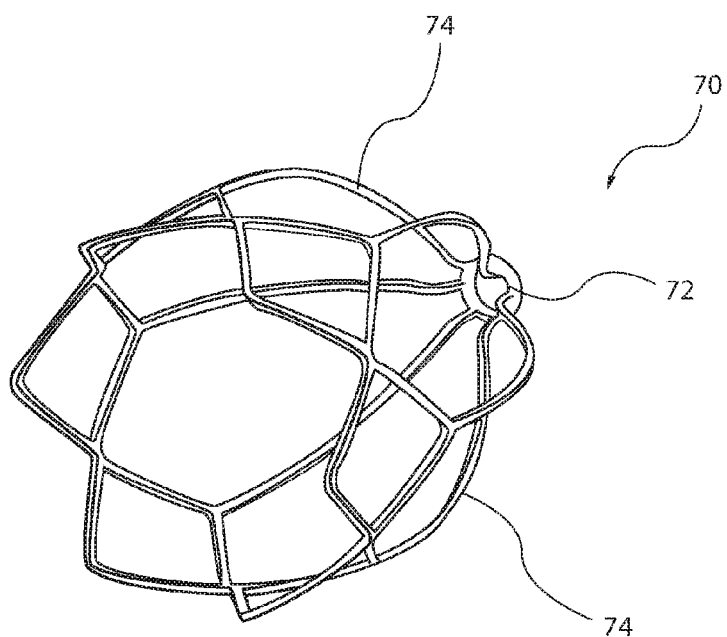

An example of support frame 70 is shown in FIGS. 5 and 6. The frame 70 is, for its major portion, shaped and sized to be consistent with the shape and size of the conical member 20. In particular, the frame 70 has a ring element 72 of dimensions equivalent to those of the collar 25, such that the ring 72 can be embedded within the volume of the collar 25. Extending from the ring 72 is a series of curved struts 74 (in the example shown there being six such struts) which have a curvature which follows that of the curvature of the conical member 20. These struts 74 are preferably evenly circumferentially spaced around the ring 72. In this embodiment, the struts 74 terminate at a diamond shaped frame element 76 formed of first and second zigzag rings 78, 80 disposed in offset relation such that the peaks 82 of the ring 78 are aligned with the troughs 84 of the ring 80. In this embodiment, the ring 80 at the extremity of the frame 70 widens radially outwardly, so as in practice to be in compression when disposed within a vessel, thereby to generate a holding force holding the frame 70 within the vessel.

The frame 70 may be made of a metal or metal alloy, in an embodiment of a shape memory material. Nitinol is a suitable material, although any other shape memory material including shape memory polymers could be used.

Figure 7:
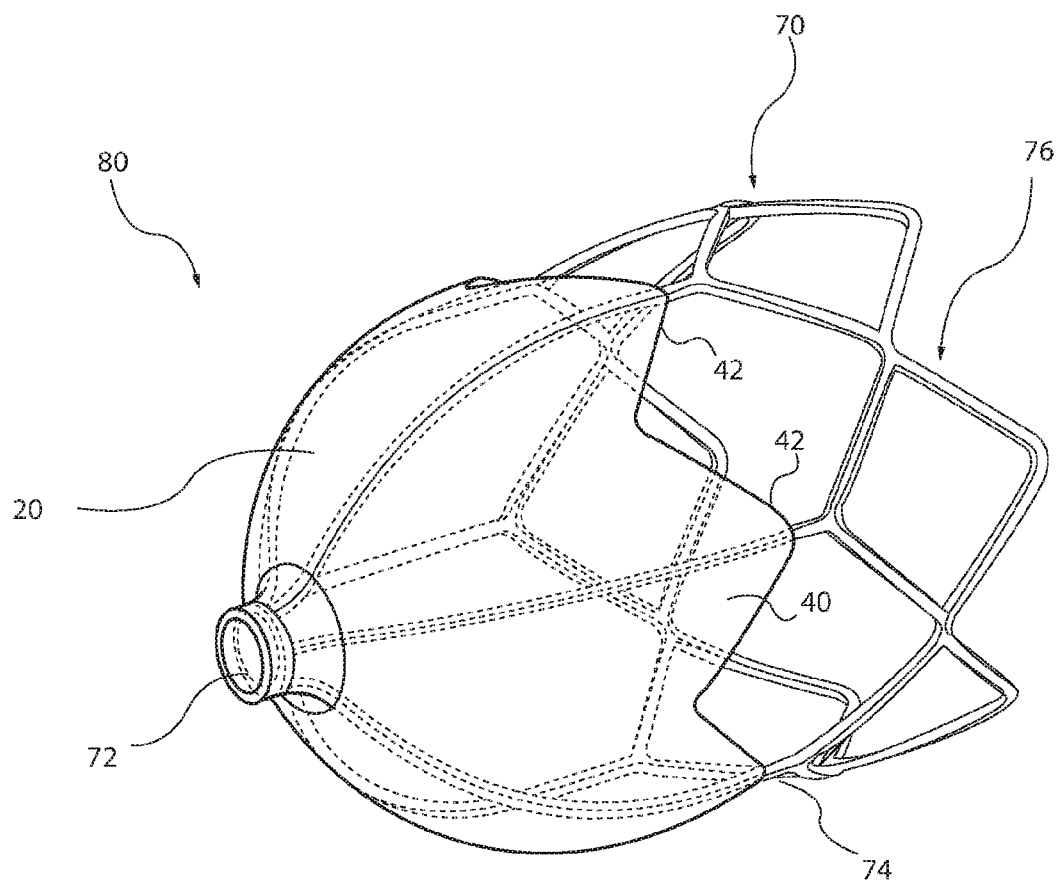
FIG. 7 is a line drawing of the frame of FIGS. 5 and 6 fitted to a conical occluder member of the type taught herein.

Referring now to FIG. 7, this shows a schematic drawing of a first arrangement 80 of the frame 70 fitted into a conical occluder member 20. As will be seen, the frame 70 nests within the occluder member 20 and is at least a tight fit thereto. In this example, the curved strut elements 74 are aligned with the toothed flanges 40 of the conical occluder member 20, such that the apices 42 of the toothed flanges 40 sit over and are supported by the curved struts 74. The diamond shaped frame extremity 76 extends beyond the conical occluder member 20 in what could be described as a bare stent arrangement.

Figure 8:
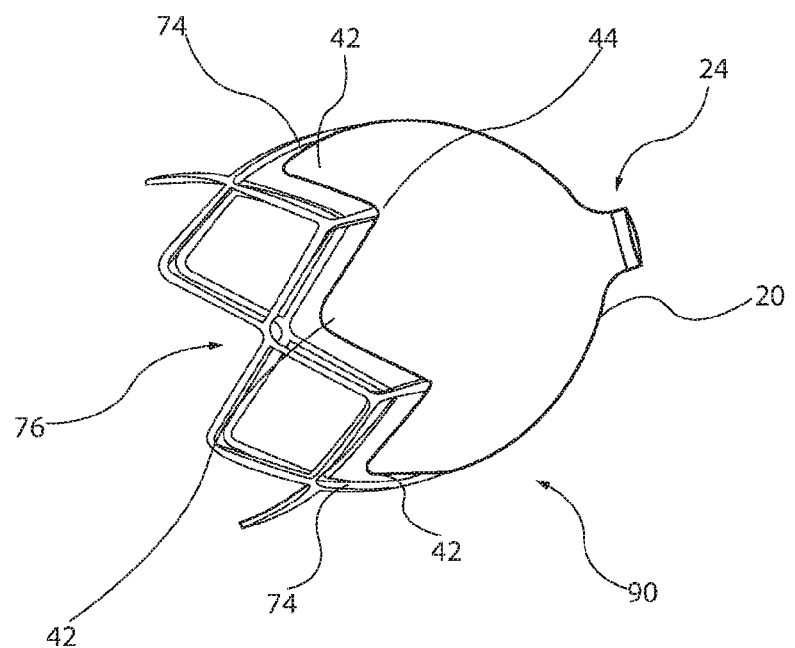
FIG. 8 is a side elevational view of an occluder element and frame combination.

Another arrangement 90 is shown in FIG. 8, in which the frame 70 is similarly disposed within the conical occluder member 20, although in this instance the strut elements 74 are aligned with the troughs 44 of the conical occluder member 20, leaving the apices 42 of the toothed flanges 40 free. Again, the diamond shaped frame element 76 extends beyond the wide end of the conical member 20, in the manner of a bare stent.

The arrangement of FIG. 8 is useful in embodiments in which the toothed flanges 40 are self-supportive and allows the flanges 40 to open out against the vessel wall, assisted by the pressure of blood within the vessel.

Figure 9:
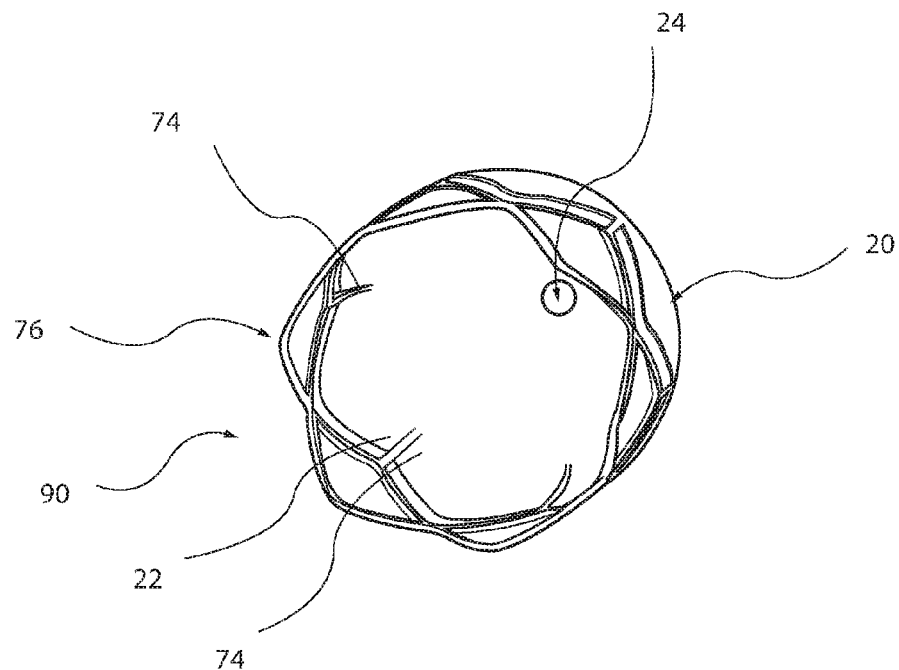
FIG. 9 is a perspective view from the wide end of a combination occluder member and frame as shown in FIG. 8.

Referring now to FIG. 9, this shows a perspective view of the assembly of FIG. 8. As can be seen in FIG. 9, the frame 70 is partially embedded within the thickness of the walls of the membrane 22 of the conical member 20. Specifically, the extremities of the curved struts 74 adjacent the diamond-shaped frame portion 76 are disposed on the inside of the member 22 and become progressively embedded within the thickness of the wall of the membrane 22 so as to become fully embedded within the membrane closer to and including at the narrow end 24 of the conical member 20. The end ring 72 is also fully embedded within the collar 25 of the conical member 20. Embedding the frame 70 in the conical member 20 in this manner reduces the overall thickness of the structure and as a result improves the compressibility of the device for delivery purposes.

Figure 10:
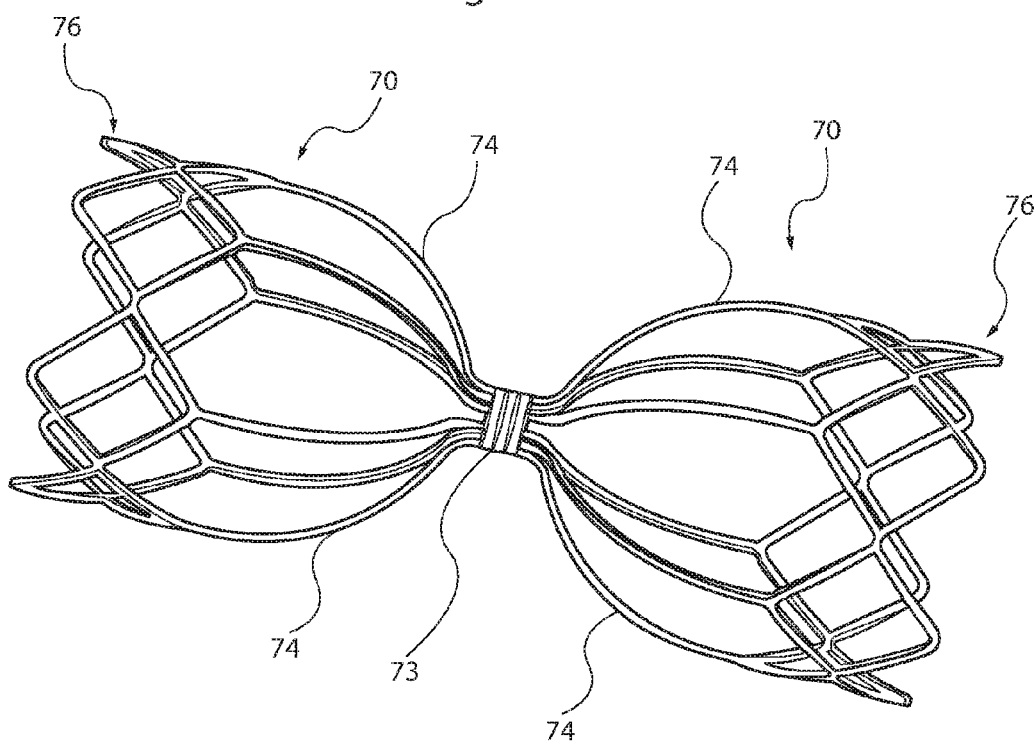
FIG. 10 is a side elevational view of an embodiment of double frame element useful for a double occluder device as shown in FIG. 4.

Referring now to FIG. 10, this shows an embodiment of frame structure suitable for a double occluder device of the type shown in FIG. 4. The structure includes first and second opposing frame elements 70 generally the same as the frame 70 shown in FIGS. 5 and 6 and which are coupled to one another by a medial constraining ring 73, which may be a common tubular or ring-like element attached to or integrally formed with the frames 70. In another embodiment, the curved struts 74 may be continuous between the two diamond-shaped end stent elements 76 and are then drawn into a radially closed configuration as shown via the constraining ring 73, disposed over the strut elements 74. It will be appreciated that in other embodiments, the medial constraining ring 73 could be of a non-ring form. It may, for example, be in the form of a coil, which would add flexibility in bending between the two frames 70.

The conical members 20 could be oriented on the double frame of FIG. 10 in either of the manners shown in FIGS. 7 and 8.

The skilled person will appreciate that the frame structure shown in FIG. 10 does not necessarily have to be used in connection with the occluder structure shown in FIG. 4. A frame is optional, in dependence upon the nature of the membrane used for the occluding members, the size of the device and the size of the vessel in which the device is to be deployed.

The occluder structure taught herein can reliably occlude a vessel and is also able to be compressed to a small diameter for deployment in or through small vessels. Furthermore, the device can provide instant occlusion of a vessel, particularly useful in many medical applications.

Silicone is a preferred material for the member of a vessel as this can provide a self-supporting structure which is able to seal well against a vessel wall and as a result prevent blood flow through the vessel and it can also prevent leakage of blood around the sides of the device.

The tooth-shaped structure at the wide end of each cup has been found to prevent the occurrence of loose flaps of occluder material as can occur with other structures of occluders. The avoidance of such loose flaps can avoid leakage problems.

The change in thickness of the membrane forming the occluder gives the conical member greater strength towards its narrow end and as a result enables it to produce greater return or opening forces from a radially constrained delivery configuration. This enables the cup to open out by itself as a result of its inherent resilience. This not only assists the occluder opening out on deployment but also enhances the occluding function.

The diamond shaped exposed stent structure which can be used in the embodiments disclosed herein provides good coupling to the vessel and as a result stable positioning of the occluder. The exposed frame elements can, over time, become embedded within the vessel wall, thereby contributing to positional stability of the device within the vessel and preventing migration of the device.

As previously explained, all of the embodiments described above with reference to FIGS. 1 to 10 are directed to an occluder. The teachings herein can be used with other implantable medical devices including, for example, filter elements. A filter element could be formed by cutting holes or apertures within the membrane 22 to allow the passage of blood plasma through the conical members 20, but with the apertures being small enough to trap debris such as plaque or thrombi.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A collapsible medical device including:
    first and second conical members, each having a wide end and a narrow end;
    a connecting element coupled to the first and second conical members, the connecting element being fixed to the narrow end of each conical member, the first and second conical members being arranged such that their narrow ends are adjacent one another and their wide ends face opposing directions;
    the first and second conical members each including a conical membrane having a thickness decreasing from the narrow end to the wide end; wherein a portion of the conical membrane at
    the wide end of each conical member comprises tooth shaped elements with a thickness that enables the tooth shaped elements to be self-supporting, such that the tooth shaped elements retain their shapes without a support or frame elements.

2. A medical device according to claim 1, wherein the device is an occluder and the membrane of the first and second conical members is an occluding element.

3. A medical device according to claim 1, wherein the conical membranes are formed of a flexible and non-degradable material.

4. A medical device according to claim 1, wherein the conical membranes are formed of a polymeric material.

5. A medical device according to claim 1, wherein the conical membranes are formed of silicone.

6. A medical device according to claim 1, including at least one frame element coupled to the conical members.

7. A medical device according to claim 6, including first and second frame elements coupled respectively to the first and second conical members.

8. A medical device according to claim 7, wherein the frame element includes a medial constraining ring disposed between the first and second conical members.

9. A medical device according to claim 6, wherein the frame element spans across the first and second conical members.

10. A medical device according to claim 6, wherein the or each frame element is made of a metal or metal alloy.

11. A medical device according to claim 6, wherein the or each frame element is made of a shape memory material.

12. A medical device according to claim 6, wherein the or each frame element extends beyond the wide ends of the conical members.

13. A medical device according to claim 12, wherein the or each frame element includes a diamond shaped portion extending beyond the wide ends of the conical members.

14. A medical device according to claim 6, wherein the or each frame element is at least partially embedded in the membrane of the conical members.

15. A medical device according to claim 1, wherein the connecting element is one of flexible and rigid.

16. A medical device according to claim 1, wherein the connecting element is a rod.

17. A medical device according to claim 1, wherein the connecting element is a cannula having a lumen therein.

18. A medical device according to claim 17, including at least one closure element disposed to close the lumen of the cannula.

19. A medical device according to claim 18, wherein the at least one closure element is an occlusion element.

* * * * *